United States Patent
Cohen et al.

(10) Patent No.: US 10,682,181 B2
(45) Date of Patent: Jun. 16, 2020

(54) METHODS AND SYSTEMS FOR MODELING AND REGISTRATION OF 3-DIMENSIONAL IMAGES OF THE HEART

(71) Applicant: Biosense Webster (Israel) Ltd., Yokneam (IL)

(72) Inventors: Benjamin Cohen, Haifa (IL); Lior Zar, Poria Illit (IL); Natan Sharon Katz, Atlit (IL); Aharon Turgeman, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 90 days.

(21) Appl. No.: 15/696,975

(22) Filed: Sep. 6, 2017

(65) Prior Publication Data
US 2019/0069954 A1 Mar. 7, 2019

(51) Int. Cl.
*A61B 5/00* (2006.01)
*A61B 18/14* (2006.01)
(Continued)

(52) U.S. Cl.
CPC .............. *A61B 34/10* (2016.02); *A61B 5/044* (2013.01); *A61B 5/04012* (2013.01); *A61B 5/0422* (2013.01); *A61B 5/04525* (2013.01); *A61B 5/6858* (2013.01); *A61B 5/6885* (2013.01); *A61B 6/463* (2013.01); *A61B 6/503* (2013.01); *A61B 6/5247* (2013.01); *A61B 18/1492* (2013.01); *A61B 90/37* (2016.02); *A61N 7/022* (2013.01); *A61B 6/032* (2013.01); *A61B 18/1206* (2013.01); *A61B 18/20* (2013.01); *A61B 2018/0022* (2013.01); *A61B 2018/00267* (2013.01); *A61B 2018/00351* (2013.01); *A61B 2018/00577* (2013.01); *A61B 2018/00791* (2013.01); *A61B 2018/00815* (2013.01); *A61B 2018/00821* (2013.01); *A61B 2018/00839* (2013.01); *A61B 2018/00875* (2013.01); *A61B 2018/00916* (2013.01);
(Continued)

(58) Field of Classification Search
CPC .............. A61B 5/6869; A61B 18/1492; A61B 2034/107
See application file for complete search history.

(56) References Cited

U.S. PATENT DOCUMENTS

| 5,738,096 A | 4/1998 | Ben-Haim |
| 6,106,466 A * | 8/2000 | Sheehan ................ A61B 5/062 128/916 |

(Continued)

OTHER PUBLICATIONS

Pending U.S. Appl. No. 15/637,191, filed Jun. 29, 2017.
(Continued)

*Primary Examiner* — William J Levicky

(57) ABSTRACT

Cardiac catheterization is carried out by inserting a multi-electrode probe into a heart, constructing a position map of the electrodes, and simulating a 3-dimensional surface of the heart. The method is further carried out by placing the position map in registration with an acquired image of the heart, constructing, based on the position map, a mesh that models the 3-dimensional surface of the heart, and adjusting positions of vertices of the mesh relative to mapped points in the position map to improve a registration of the mesh with the acquired image.

19 Claims, 8 Drawing Sheets

(51) Int. Cl.

| | |
|---|---|
| *A61B 34/20* | (2016.01) |
| *A61B 34/10* | (2016.01) |
| *A61B 5/042* | (2006.01) |
| *A61B 5/044* | (2006.01) |
| *A61B 5/04* | (2006.01) |
| *A61B 6/00* | (2006.01) |
| *A61B 5/0452* | (2006.01) |
| *A61B 90/00* | (2016.01) |
| *A61N 7/02* | (2006.01) |
| *A61B 18/00* | (2006.01) |
| *A61B 18/12* | (2006.01) |
| *A61B 18/20* | (2006.01) |
| *A61B 6/03* | (2006.01) |

(52) U.S. Cl.
CPC .  *A61B 2034/105* (2016.02); *A61B 2034/2051* (2016.02); *A61B 2034/2053* (2016.02); *A61B 2090/064* (2016.02); *A61B 2090/365* (2016.02); *A61B 2090/374* (2016.02); *A61B 2090/3762* (2016.02); *A61B 2218/002* (2013.01); *A61N 7/02* (2013.01)

(56) References Cited

U.S. PATENT DOCUMENTS

| | | | |
|---|---|---|---|
| 6,226,542 B1* | 5/2001 | Reisfeld | A61B 5/04011 |
| | | | 600/407 |
| 6,301,496 B1 | 10/2001 | Reisfeld | |
| 6,650,927 B1* | 11/2003 | Keidar | A61B 5/062 |
| | | | 600/424 |
| 6,814,733 B2 | 11/2004 | Yitzhack Schwartz et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 7,517,318 B2 | 4/2009 | Altmann et al. | |
| 7,536,218 B2 | 5/2009 | Govari et al. | |
| 7,756,576 B2 | 7/2010 | Levin | |
| 8,320,711 B2 | 11/2012 | Altmann et al. | |
| 8,428,700 B2 | 4/2013 | Doron Harley et al. | |
| 8,478,383 B2 | 7/2013 | Bar-Tal et al. | |
| 8,768,022 B2 | 7/2014 | Miga et al. | |
| 8,819,591 B2 | 8/2014 | Wang et al. | |
| 2006/0159323 A1 | 7/2006 | Sun et al. | |
| 2006/0173251 A1 | 8/2006 | Govari et al. | |
| 2007/0038078 A1 | 2/2007 | Osadchy | |
| 2007/0049817 A1* | 3/2007 | Preiss | A61B 5/06 |
| | | | 600/407 |
| 2008/0275465 A1 | 11/2008 | Paul et al. | |
| 2008/0288038 A1 | 11/2008 | Paul et al. | |
| 2015/0164356 A1 | 6/2015 | Merschon et al. | |
| 2016/0063670 A1* | 3/2016 | Wilensky | H04N 5/23229 |
| | | | 348/578 |
| 2016/0120426 A1 | 5/2016 | Urman et al. | |
| 2017/0079738 A1 | 3/2017 | Botzer et al. | |
| 2017/0103570 A1 | 4/2017 | Zar et al. | |
| 2017/0127974 A1 | 5/2017 | Bonyak et al. | |
| 2017/0221254 A1 | 8/2017 | Zar et al. | |

OTHER PUBLICATIONS

European Search Report dated Jan. 24, 2019 from corresponding European Patent Application No. 18192728.6.

Alessandrini, Martino et al, "An Automatic Framework for the Non-rigid Alignment of Electro:anatomical Maps and Preoperative Anatomical Scans in Atrial Fibrillation", 2016 Computing in Cardiology Conference (CINC), vol. 43, Sep. 14, 2016.

Rettmann, Maryam E. et al., "Quantitative Modeling of the Accuracy in Registering Preoperative Patient-Specific Anatomic Models into Left Atrial Cardiac Ablation Procedures", Medical Physics, AIP, Melville, NY, US, vol. 41, No. 2, Feb. 1, 2014, pp. 021909-3, col. 2.

Zhong, Hua et al, "An Improved Algorithm for Intraoperative Registration of Computed Tomographic Left Atrial Images", Europace, vol. 13, No. 3, Nov. 17, 2010, pp. 383-388.

* cited by examiner

METHODS AND SYSTEMS FOR MODELING AND REGISTRATION OF 3-DIMENSIONAL IMAGES OF THE HEART

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to image data processing. More particularly, this invention relates to modeling and registration of 3-dimensional images of the heart.

2. Description of the Related Art

Medical catheterizations are routinely carried out today, for example, in cases of cardiac arrhythmias, such as atrial fibrillation, which occur when regions of cardiac tissue abnormally conduct electric signals to adjacent tissue, thereby disrupting the normal cardiac cycle and causing asynchronous rhythm. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions. It is desirable in such procedures to provide a convenient representations of the cardiac anatomy to the operator.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity, such as local activation times (LAT) at multiple sampled points in the heart chamber.

For example, commonly assigned U.S. Patent Application Publication No. 2017/0103570 to Zar et al., which is herein incorporated by reference, discloses 3-dimensional cardiac reconstruction is carried out by catheterizing a heart using a probe with a mapping electrode, and acquiring electrical data from respective locations in regions of interest in the heart, representing the locations of the electrical data as a point cloud, reconstructing a model of the heart from the point cloud, applying a set of filters to the model to produce a filtered volume, segmenting the filtered volume to define components of the heart, and reporting the segmented filtered volume.

U.S. Pat. No. 8,428,700 to Harley et al., proposes generating an electroanatomic representation of a patient's heart based on the signals measured at the electrodes and information about the positions of the electrodes. The method includes performing a catheter registration procedure with other imaging modalities, such as MRI, annotating the measured signals, and adjusting the annotations for other measured signals in spatial proximity to the specified measured signal.

SUMMARY OF THE INVENTION

A typical catheterization session involves registration of a scanned CT/MRI image with a 3-dimensional electroanatomic map. However, after registration there are still differences between the CT/MRI image and the real time anatomy determined in a current position map. During the procedure real-time catheter positions are established, and it is verified that the catheter electrodes are in contact with the heart wall, for example by a force threshold measurement or by tissue proximity indications. The current position map is registered with a CT/MRI image.

A mesh fitting algorithm to identify and resolve the differences in real-time. A 3-dimensional matrix is constructed to model the current position map. Points on the matrix are then adjusted to more closely approximate points on the current position map.

There is provided according to embodiments of the invention a method, which is carried out by inserting a multi-electrode probe into a heart, constructing a position map of the electrodes, and simulating a 3-dimensional surface of the heart. The method is further carried out by placing the position map in registration with an acquired image of the heart, constructing, based on the position map, a mesh that models the 3-dimensional surface of the heart, and adjusting positions of vertices of the mesh relative to mapped points in the position map to improve a registration of the mesh with the acquired image.

According to a further aspect of the method, the mesh is a triangular matrix.

In one aspect of the method adjusting positions of the vertices includes identifying all vertices of the mesh that are within a predetermined distance from a selected mapped point, calculating respective weight factors based on distances between the identified vertices and the selected mapped point, calculating new positions for the identified vertices that represent a shift toward the selected mapped point according to the respective weight factors, and defining a new mesh based on the new positions.

According to yet another aspect of the method, the respective weight factors are calculated according to an inverse square of the distances between the identified vertices and the selected mapped point.

In still another aspect of the method, the new positions are determined as a vector sum of shifts toward respective mapped points determined in performances of identifying all vertices and calculating new positions.

According to an additional aspect of the method, the distances between the identified vertices and the selected mapped point are geodesic distances.

According to another aspect of the method, inserting a probe includes ascertaining tissue contact of the electrodes and a wall of the heart.

There is further provided according to embodiments of the invention an apparatus, including a multi-electrode probe adapted for insertion into a heart of a living subject, and a processor, which is configured to receive an electrical signal from the electrodes and to perform the steps of: constructing a position map of the electrodes, simulating a 3-dimensional surface of the heart, placing the position map in registration with an acquired image of the heart, constructing, based on the position map, a mesh that models the 3-dimensional surface of the heart, and adjusting positions of vertices of the mesh relative to mapped points on the position map to improve a registration of the mesh with the acquired image.

There is further provided according to embodiments of the invention a computer software product including a non-transitory computer-readable storage medium in which computer program instructions are stored, which instructions, when executed by a computer, cause the computer to perform the steps of: constructing a position map of the electrodes, simulating a 3-dimensional surface of the heart, placing the position map in registration with an acquired image of the heart, constructing, based on the position map, a mesh that models the 3-dimensional surface of the heart, and adjusting positions of vertices of the mesh relative to mapped points on the position map to improve a registration of the mesh with the acquired image.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview.

Figure 1:
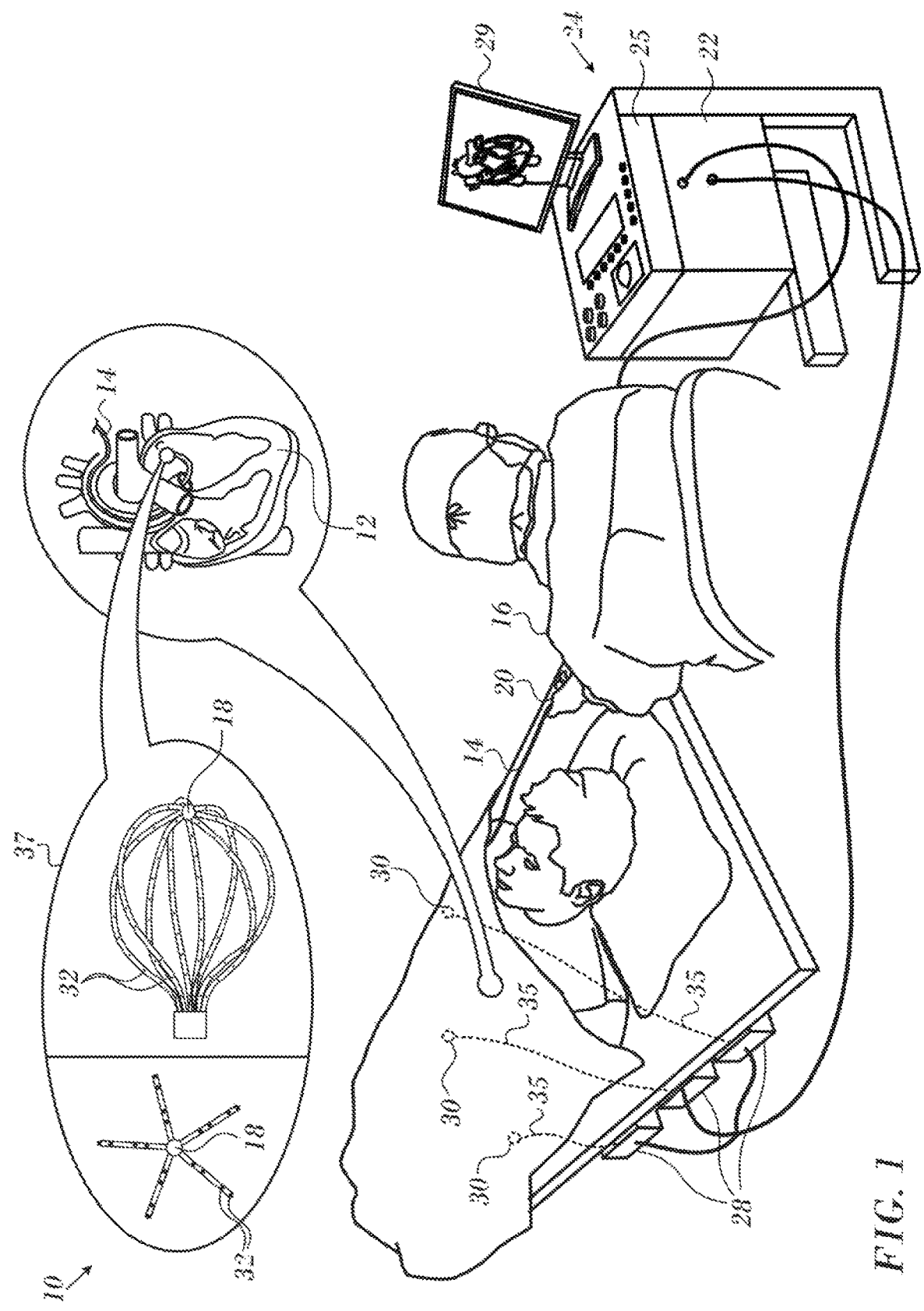
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a balloon or basket catheter as shown in the right portion of balloon 37, or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images.

Figure 2:
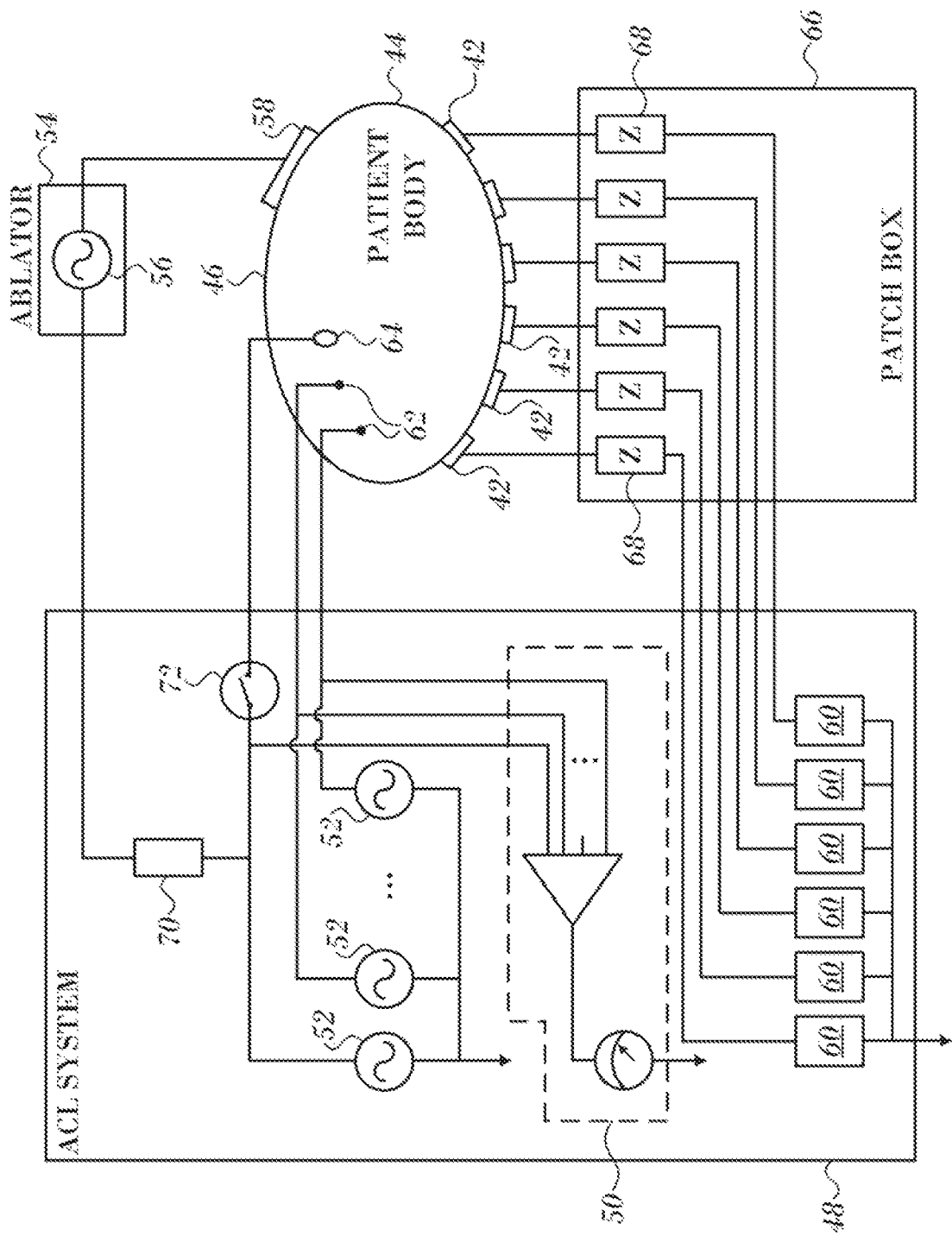
FIG. 2 is a schematic diagram of an ablation and active current location (ACL) circuit in accordance with an embodiment of the invention.

Reference is now made to FIG. 2, which is a schematic diagram of an ablation and active current location (ACL) circuit for use with the system shown in FIG. 1. This arrangement is similar to that described in U.S. Patent Application Publications 2006/0173251, to Govari et al., and 2007/0038078, to Osadchy, which are herein incorporated by reference. The arrangement can be modified to operate in accordance with the principles of the present invention. A brief description follows for convenience of presentation.

A plurality of body surface electrodes 42, which can be adhesive skin patches, are coupled to a body surface 44 (e.g., the skin) of subject 46. The body surface electrodes 42 are sometimes referred to herein as "patches". In cardiac applications the body surface electrodes 42 are usually distributed so as to surround the heart, three on the chest of the subject and three on the back. However, the number of the body surface electrodes 42 is not critical, and they may be placed at convenient locations on the body surface 44 in the general vicinity of the site of the medical procedure.

A control unit 48, normally disposed in the console 24 (FIG. 1), includes current measurement circuitry 50 and one or more catheter electrode transmitters 52 for driving a current through one or more of the electrodes 42 to one or more of the body surface electrodes 42 at respective working frequencies. The control unit 48 is linked to a positioning processor (FIG. 1). The control unit 48 is linked to an ablator 54, which comprises at least one ablation generator 56. Currents through the body surface electrodes 42 and an ablator body surface electrode 58 flow in a circuit with the ablation generator 56 and are measured by respective current measurement circuits that are disposed within body electrode receivers 60, sometimes referred to herein as "patch measurement circuits". The body electrode receivers 60 are typically incorporated in the control unit 48. Alternatively, they may be affixed to the body surface electrodes 42. Catheter electrodes are represented as measurement electrodes 62 (circles) and a dual-purpose electrode 64 (ellipse). The dual-purpose electrode 64 functions as an ablation electrode and also serves as one of the measurement electrodes.

The body surface electrodes 42 are connected to the body electrode receivers 60 via a patch box 66, which protects the system from ablation and defibrillation currents. Typically the system is configured with six body electrode receivers 60. The patch box parasitic impedances 68 (Z), are measured during production and thus known a priori. These impedances are discussed below.

Typically, although only two measurement electrodes 62 are shown for convenience, about 80 measurement electrodes are used for impedance measurements. Typically there are one or two ablation electrodes. The coordinates of a catheter inside the body are determined in the positioning system by passing currents between electrodes on the catheter and the body surface electrodes 42.

The control unit 48 may also control an ablation circuit, comprising ablator 54, and the dual-purpose electrode 64. The ablator 54 is typically disposed externally to the control unit 48 and incorporates the ablation generator 56. It connects with the ablator body surface electrode 58 and to an ablator filter 70, which in this example is shown within the control unit 48. However this location is not essential. A switch 72 configures the ablator circuit for different modes of operation as described below. Voltage measurement circuitry is provided for determining the output of the catheter electrode transmitters 52. It will be noted from inspection that the ablation circuit is connected to one of the catheter electrode transmitters 52.

Figure 3:
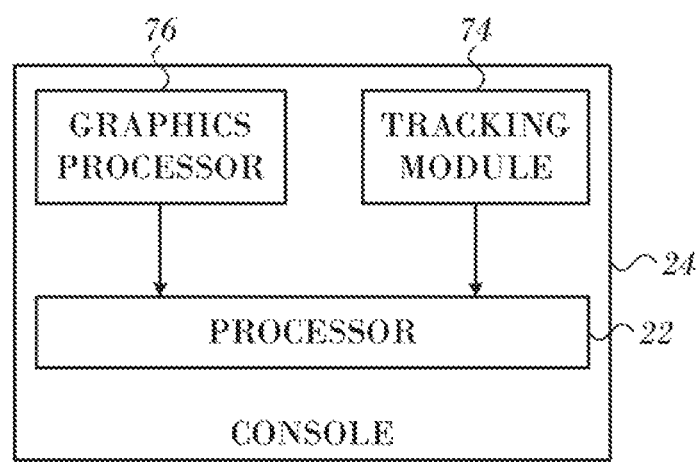
FIG. 3 is a block diagram of aspects of a processor in accordance with an embodiment of the invention.

Reference is now made to FIG. 3, which is a block diagram of aspects of the processor 22 in accordance with an embodiment of the invention. Typically the processor 22 is located in the console 24 (FIG. 1), but it can be remote or distributed among several sites. The processor 22 may use a tracking module, such as tracking module 74, to convert signals from the above-noted location-sensing devices to location coordinates in a 3-dimensional frame of reference defined by the field generating coils 28 (FIG. 1). Processor 22 is linked to a graphics processor 76. The graphics processor 76 is a parallel processing unit that usually has approximately 2,000 processors.

Figure 4:
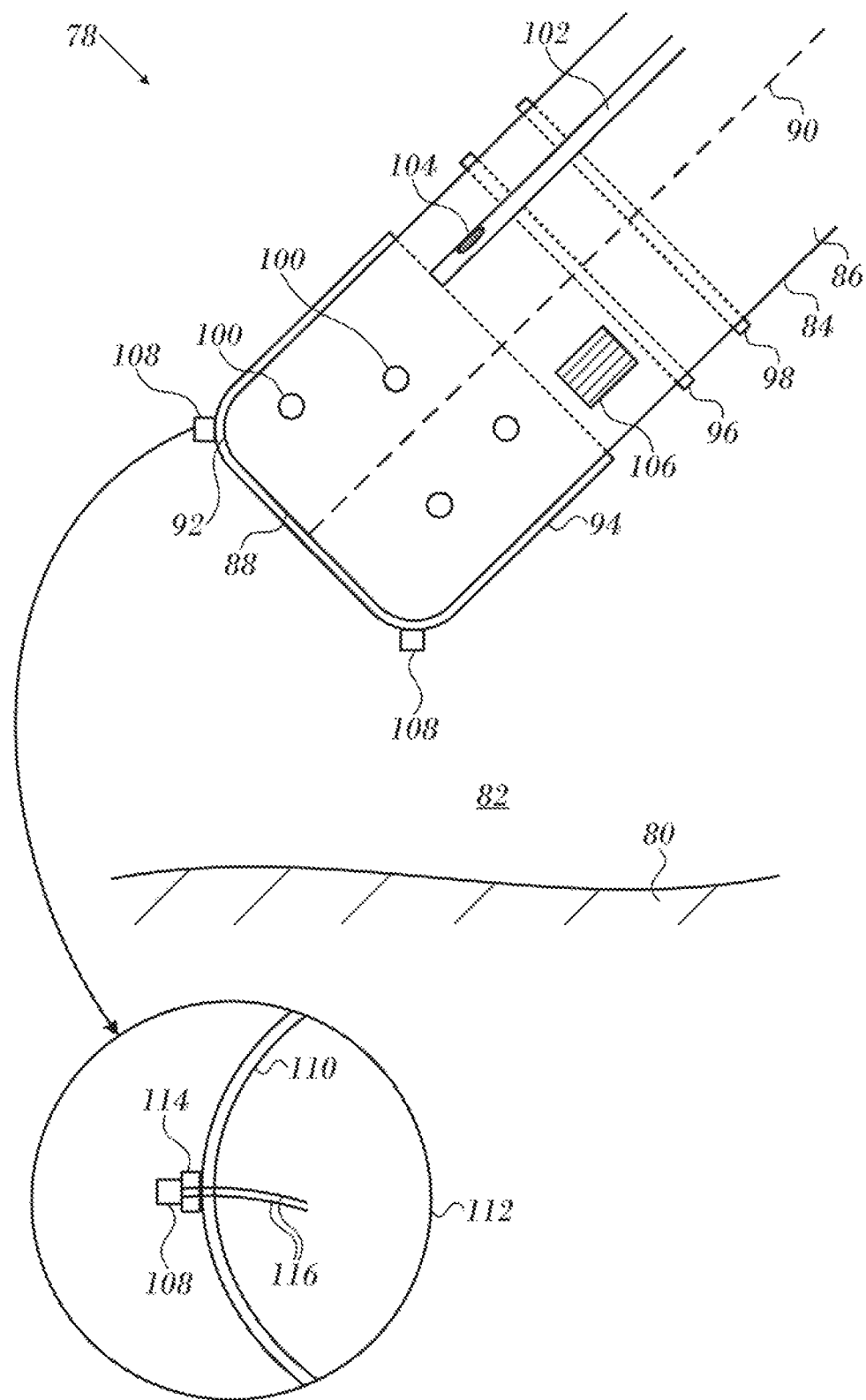
FIG. 4 is a sectional view along the length of the distal segment of a cardiac catheter, in accordance with an embodiment of the invention.

In order determine the location of the electrodes with respect to the wall of the heart, it is necessary to ascertain tissue contact. One useful technique is a thermometry-based method as shown in FIG. 4, which is a sectional view along the length of distal segment 78 of a cardiac catheter in accordance with an embodiment of the invention. The distal segment 78 is in proximity to tissue 80, and is assumed to be immersed in fluid 82, so that tissue 80 has a surface 29 contacting the fluid. Fluid 82 typically comprises a mixture of blood and saline solution. By way of example, distal segment 78 is assumed herein to be formed from an insulating substrate 84 in the shape of a cylinder 86 closed by a generally flat surface 88 at one end. Cylinder 86 has an axis of symmetry 90. A curved section 92 joins flat surface 88 and cylinder 86. A typical diameter of cylinder 86 is 2.5 mm, and a typical radius of the curved section 92 is 0.5 mm.

Distal segment 78 comprises three electrodes 94, 96, 98, the electrodes being insulated from each other. The electrodes 94, 96, 98 typically comprise thin metal layers formed over insulating substrate 84. Typically, the distal tip has other electrodes, insulated from the electrodes 94, 96, 98, which for simplicity are not shown in the diagram. Tip electrode 94 has the shape of a cup with a flat base, and is herein also referred to as the cup electrode. Cup electrode 94 typically has a thickness in a range from approximately 0.1 mm to approximately 0.2 30 mm. Second and third electrodes 94, 96, are usually in the form of rings, and are also known as ring electrodes.

Electrodes 94, 96, 98 are connected to a controller in console 24 (FIG. 1) by wires (not shown). At least one of the electrodes is used to ablate tissue 80. Typically, during ablation, heat is generated in the ablating electrode and in the surrounding region. In order to dissipate the heat, small irrigation apertures 100 in the cup electrode. The apertures 100 typically have diameters in an approximate range 0.1-0.2 mm. An irrigation tube 102 supplies saline solution to the apertures 100, and the rate of flow of the saline solution through the apertures 100 (causing fluid 82 to be a mixture of blood and saline solution) is controlled by an irrigation module (not shown) in the console 24 (FIG. 1). The saline rate of flow is typically in the range of approximately 2-20 cc/minute, but may be higher or lower than this range.

A saline temperature sensor 104, typically a thermocouple, is located in tube 102, and provides a signal to circuitry in the console 24 (FIG. 1) module 56 enabling the console 24 to measure a temperature of the saline solution input to apertures 100. While the saline solution may be provided at room ambient temperature, e.g., in a range of approximately 19-25° C., the solution may be heated slightly during its flow through the catheter, so that the final irrigation temperature may be slightly higher.

Typically, one or more location sensing devices 106 are incorporated in the distal tip. Devices 106 are configured to provide signals to the processor 22 (FIG. 1) enabling the system to ascertain the position and/or orientation of distal segment 78, In one embodiment distal segment 78 comprises one or more generally similar temperature sensors 108 (by way of example, two are shown in the diagram), which are fixedly connected, by an insulator, to the outer surface of cup electrode 94, so as to protrude from the surface. Sensors 108 have a typical diameter of approximately 0.3 mm and a length of 10 approximately 1.5 mm. In one embodiment sensors 108 are thermistors NTC Type AB6, produced by General Electric Company of Schenectady, N.Y. In an alternative embodiment, sensors 108 comprise "F" type thermistors produced by Semitec USA Corporation of Torrance, 15 California. By way of example, the following description assumes there are three sensors 108 symmetrically distributed with respect to axis 51, and located on a curved section 110 of the cup electrode. Curved section 110 of the cup electrode overlays curved section 92 of the 20 distal tip. Curved section 110 is in the shape of a partial toroid, typically a partial torus having a tube radius of approximately 0.5 mm.

A magnified section 112 of FIG. 4 illustrates one of sensors 108 in more detail. As shown in section 112, an insulator 114 separates sensors 108 from curved section 110 of the cup electrode 94. Insulator 114 is selected to provide good thermal and electrical insulation, and in some embodiments insulator 114 may comprise an adhesive that bonds sensors 108 to curved section 110. Wires 116 connect sensors 108 to the console 24 (FIG. 1).

By having sensors 108 protrude from the outer surface of cup electrode 94, the sensors 108 are able to intimately contact tissue 80. The processor 22 (FIG. 1) is thus able to use signals from the sensors 108 to provide direct temperature measurements of the tissue 80 In one embodiment the sensors 108 protrude from the outer surface of the electrode 94 by no more than 0.7 mm, and typically by approximately 0.5 mm.

Additional details of thermometry based determination of tissue contact are found in commonly assigned U.S. Patent Application Publication No. 20170079738, which is herein incorporated by reference. Alternatively, tissue contact can be determined using a contact force sensor as described, for example, in commonly assigned U.S. Patent Application Publication No. 20170127974, which is herein incorporated by reference. Further alternatively tissue contact can be determined using impedance-based methods as described U.S. Patent Application Publication Nos. 2008/0288038 and 2008/0275465, both by Sauarav et al., which are herein incorporated by reference, or using ultrasonic transducers, as described in copending, commonly assigned application Ser. No. 15/637,191, which is herein incorporated by reference. The methods may be combined with other filters, for example respiratory gating to exclude artefacts.

Figure 5:
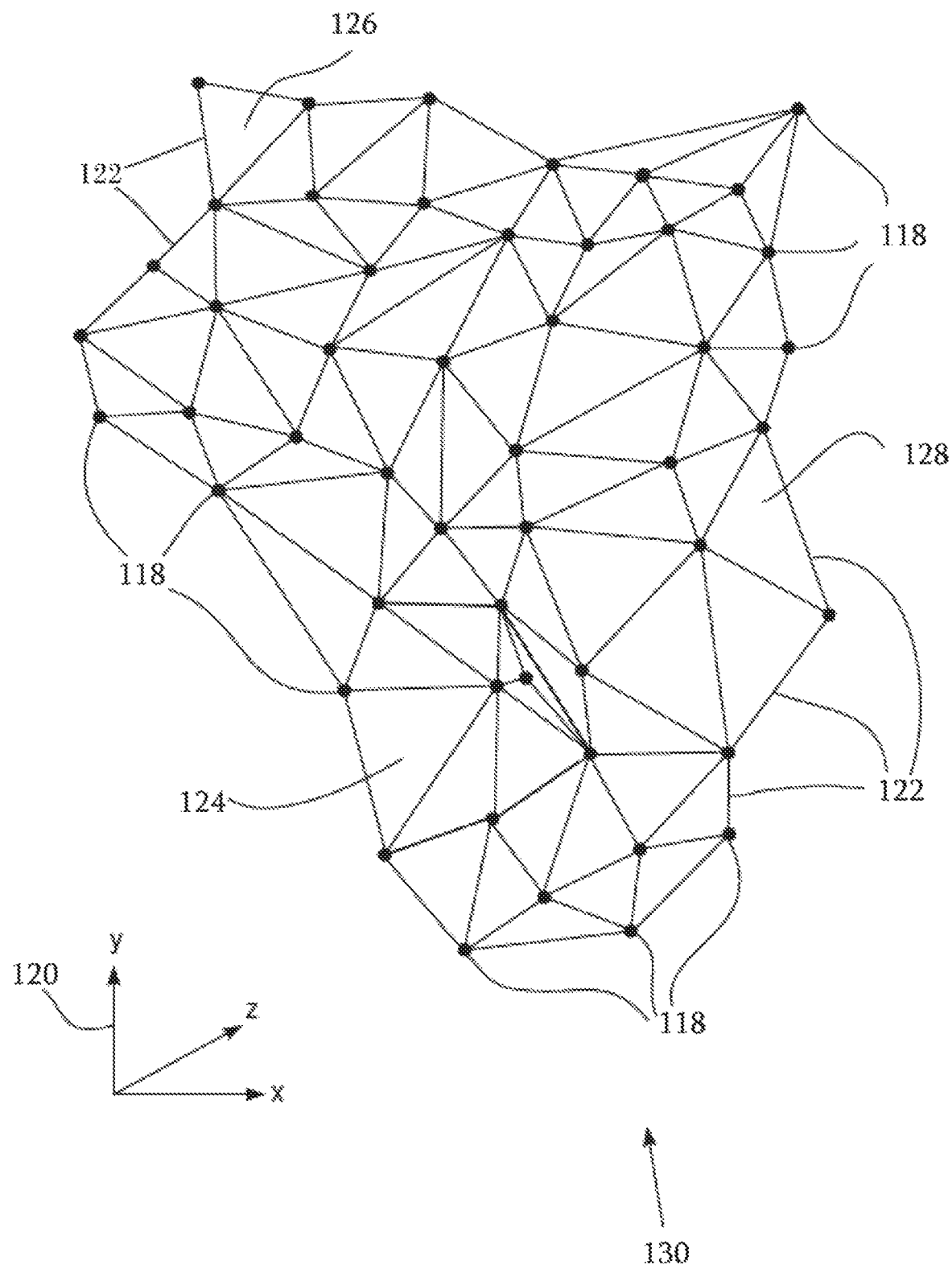
FIG. 5 is a schematic illustration of a mesh in accordance with an embodiment of the invention.

Reference is now made to FIG. 5, which is a schematic illustration of points 118 of a mesh in accordance with an embodiment of the invention. Points are registered by electrodes 32 (FIG. 1), when in contact with the endocardial surface of the heart 12. Typically during the mapping referred to above, processor 22 initially stores 3-dimensional coordinates of points 118 as measured in a 3-dimensional frame of reference 120 defined by the field generating coils 28. The processor 22 then connects 3-dimensional coordinates of points 118, herein also termed 3-dimensional vertices, by line segments 122 to produce a set of connected 3-dimensional triangles, e.g., triangles 124, 126, 128. The procedures described in commonly assigned U.S. Patent Application Publication No. 20150164356, entitled Dynamic Feature Rich Anatomical Reconstruction from a Point Cloud, which is herein incorporated by reference, may be used to produce a mesh 130. Other suitable algorithms include the ball-pivoting algorithm to produce the mesh 130. Typically, if the ball-pivoting algorithm is used, a size of the ball is set to correspond to the size of the voxels referred to below. Alternatively, the mesh may be generated as a Delaunay triangulation. Elements of the mesh each have 3-dimensional coordinates.

In one application the triangular mesh 130 models the endocardial surface. The processor 22 (FIG. 3) uses the graphics processor 76 to render the mesh 130 into an image for display on the monitor 29 (FIG. 1).

Initially, realtime positions on the mesh 130 are placed in registration with an image of the heart that was obtained by other modalities, such as computed tomography or magnetic resonance imaging (referred to herein as a "CT/MRI image"). Once this is done points of interest may be transformed from coordinates of the image to coordinates of the mesh 130.

Figure 6:
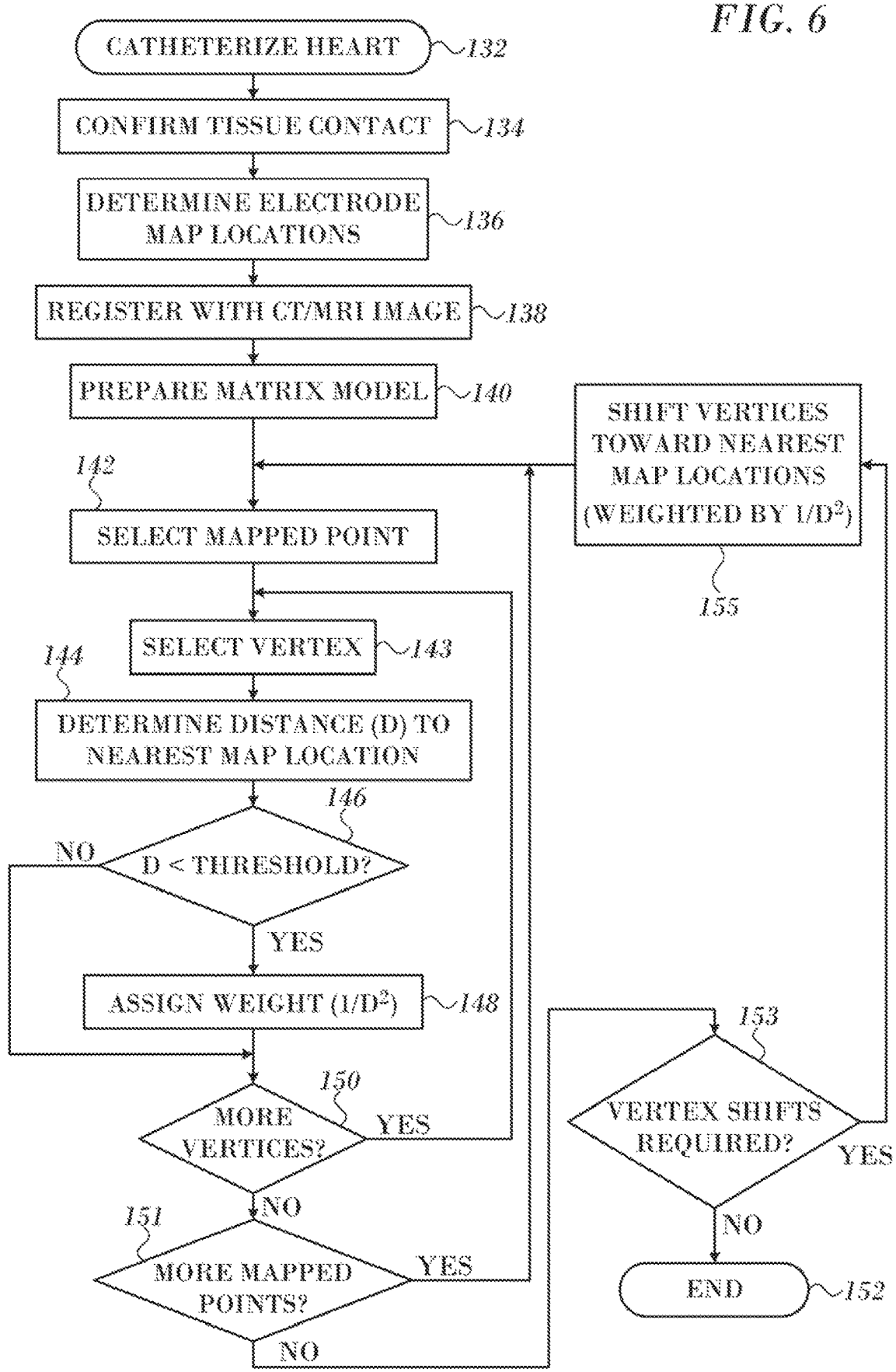
FIG. 6 is a flow chart of a method of fitting a 3-dimensional model of a heart to a CT/MRI image in accordance with an embodiment of the invention.

Nevertheless, residual differences between the CT/MRI image and the mesh remain after the registration procedure. These differences are reduced according to embodiments of the invention. Reference is now made to FIG. 6, which is a flow chart of a method of fitting a 3-dimensional model of a heart to a CT/MRI image in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method. The algorithm comprises:

For each mapped point, preferably filtered by cardiorespiratory gating:

1. Identify all the vertices in the original mesh that are within a specified radius from the filtered point.

2. For each identified vertex calculate a weight factor based on its distance to the filtered point. In one embodiment the weight factor is the inverse square of the distance 3. Shift each identified vertex towards the filtered point by the weight calculated in step 2.

At initial step 132 the heart is catheterized conventionally, typically with a multi-electrode mapping catheter, such as a balloon or basket catheter in which the electrodes have known locations on the basket or spline, and have known relationships to one another.

Next, at step 134 it is ascertained that the electrodes are in contact with the wall of the heart, using one of the above-described methods. After completion of step 134 current readings are taken at step 136 to determine the locations of the electrodes in current position map in order to construct a current position map that identifies the location of each of the electrodes 32 in the heart. One method for generation of a current position map employs the circuitry shown in FIG. 2. Details are described in the above-noted U.S. Pat. No. 8,478,383.

Next, at step 138 the current position map is placed in registration with a CT/MRI image. The teachings of U.S. Pat. Nos. 7,517,318 and 8,320,711 and in U.S. Patent Application Publication No. 20160120426, all of which are commonly assigned and herein incorporated by reference, may be used to accomplish this step. Alternatively, the CARTOMERGE™ module and other facilities of the above-noted CARTO system can accomplish this step using images of the heart prepared at the same or a different session.

Next, at step 140 a 3-dimensional model, for example the triangular mesh 130 (FIG. 5), is prepared based on the ACL readings and the current position map. This can be accomplished using the teachings of the above-noted U.S. Patent Application Publication No. 20150164356. Vertices of the matrix are assigned mapping coordinates corresponding to the electrodes of the catheter 14.

Next a mesh-fitting algorithm is performed. For each vertex in the mesh all mapped points within a geodesic distance GD are identified and respective weights for the mapped points (1/GD^2) assigned with respect to that vertex. A mapped point may lie within an influence radius of a more than one vertex, in which case respective weights for the vertices are assigned for that mapped point. The vertices are shifted toward mapped points within respective influence radii in accordance with the assigned weights. The actual shift of a vertex can be represented as a 3-dimensional vector sum.

The algorithm is repeated so long as significant changes in the vertices continue to occur, or some other termination criterion is reached.

At step 142 a mapped point is selected. All original vertices within a predefined distance, typically 2-15 mm, of the current mapped point will be evaluated in the following steps. "Original vertices" refers to the positions of the vertices at the beginning of the current iteration of the algorithm.

At step 143 an original vertex of the mesh 130 is chosen. Then, at step 144 a geodesic distance to the closest corresponding map location (in an appropriately transposed 3-dimensional coordinate system) is determined.

Next, at decision step 146, it is determined if the distance determined in step 144 is less than the predetermined distance. If the determination at step 144 is affirmative, then control proceeds to step 148. Weights are assigned according to the inverse square of the distance between the vertex and the map location.

After performing step 148 or if the determination at decision step 146 is negative, then at decision step 150, it is determined if more vertices need to be adjusted. If the determination at decision step 150 is affirmative, then control returns to step 143 to iterate the loop.

If the determination at decision step 150 is negative then, at decision step 151 it is determined if more mapped points remain to be evaluated. If the determination at decision step 151 is affirmative, then control returns to step 142.

If the determination at decision step 151 is negative, then at decision step 153 it is determined if vertex shifts are required, i.e., whether the algorithm has converged so that all required shifts are less than some minimal value, or some other termination condition has occurred, e.g., a given number of iterations have been performed.

If the determination at decision step 153 is negative then, the procedure ends at final step 152. Otherwise, the calculated shifts are carried out at step 155. The mesh 130 is adjusted by shifting the vertices toward the corresponding map locations in accordance with the assigned weights. Control then returns to step 142 to iterate the algorithm using the new mesh positions.

Figure 7:
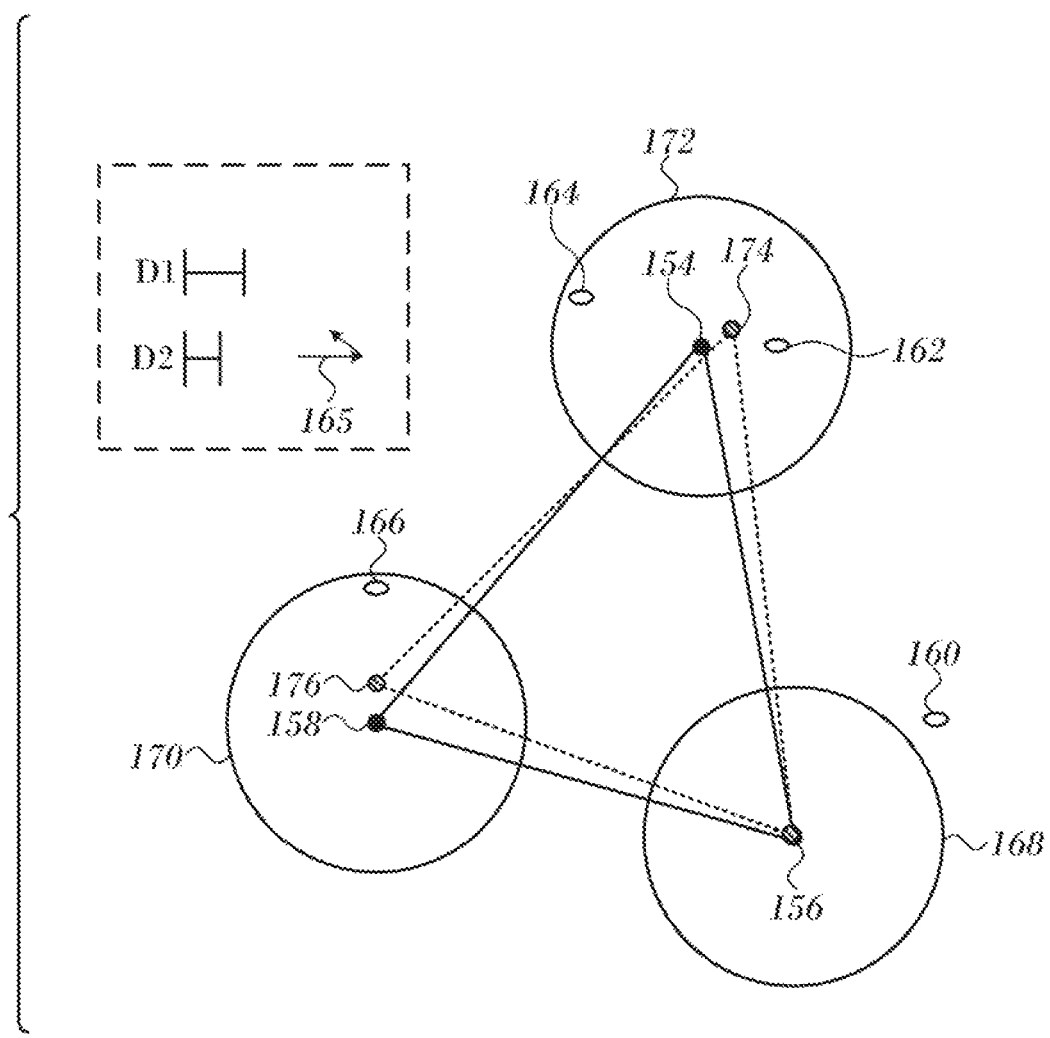
FIG. 7 is a schematic diagram of a portion of a triangular mesh can be processed in accordance with an embodiment of the invention.

Reference is now made to FIG. 7, which is a schematic diagram of a portion of a triangular mesh can be processed in accordance with an embodiment of the invention. The mesh as originally constructed in step 140 (FIG. 6) has vertices 154, 156, 158. Mapped points according to the ACL, which has been placed in registration with a CT/MRI image are indicated as points 160, 162, 164, 166. The radii of identical circles 168, 170, 172 centered on the vertices 154, 156, 158 represent the maximum distance between the vertices and the mapped points that produce a shift in the vertices.

Points 162, 164 and vertex 154 lie within circle 172. However, point 162 is closer than point 164 to vertex 154. Accordingly vertex 154 is shifted toward point 162 a distance D1, and vertex 154 assumes a first new position. Point 164 is also within the circle 172. Therefore a new weighting is calculated based on the original distance between the point 164 and vertex 154. A second shift in the direction of point 164 is performed. The final position 174 is equivalent to the sum of weighted vectors directed from vertex 154 toward point 162 and from vertex 154 toward point 164 as indicated by vector diagram 165.

The distance between vertex 156 and the closest mapped point 160 exceeds the radius of circle 168. Vertex 156 is therefore not shifted.

Vertex 158 and point 166 lie within circle 170. It will be noted that point 166 is nearly at the boundary of circle 170, while the point 162 is relatively closer to the vertex 154, being approximately half-way between the vertex 154 and the boundary of circle 172. Vertex 158 is shifted toward point 166 by a distance D2 to a position 176. The distances D1 and D2 are aligned at the left of the figure. It is evident that distance D2 is less that than distance D1.

The adjusted matrix is indicated by broken lines joining the positions 174, 176 and the vertex 156.

It will be apparent that when a vertex is shifted, its neighbors are also affected. This effect can be seen in FIG. 8 and FIG. 9, which show a portion of a matrix 178 that simulates a portion of a 3-dimensional surface of a heart in registration with a mapped point 180. Vertex 182 is the closest vertex to the mapped point 180.

Figure 8:
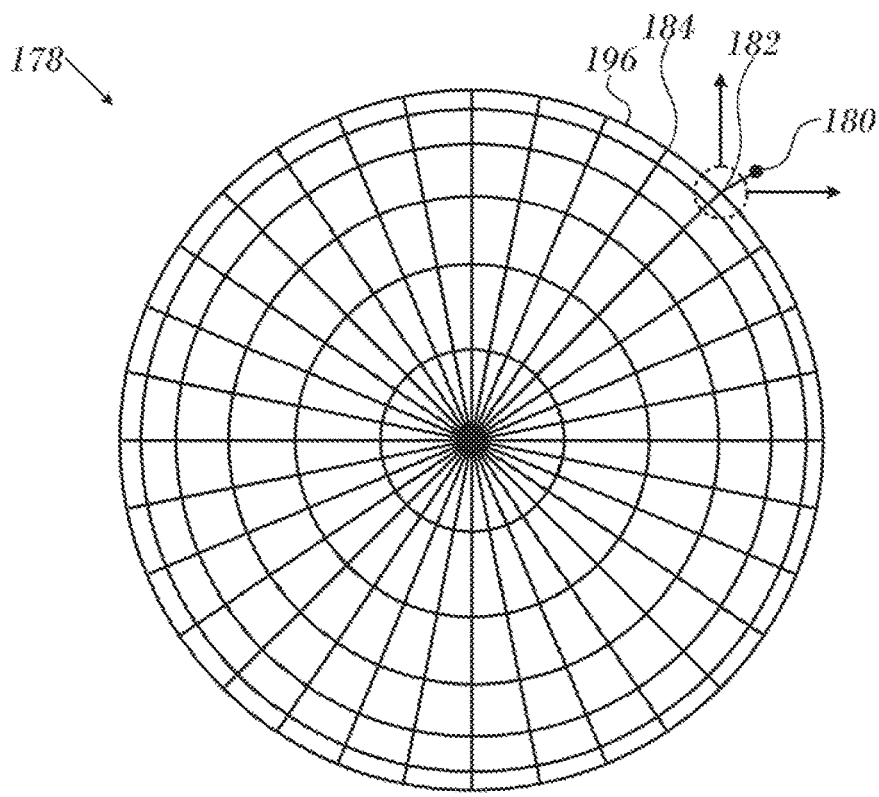
FIG. 8 shows a simulated matrix in registration with a mapped point in accordance with an embodiment of the invention.
Figure 9:
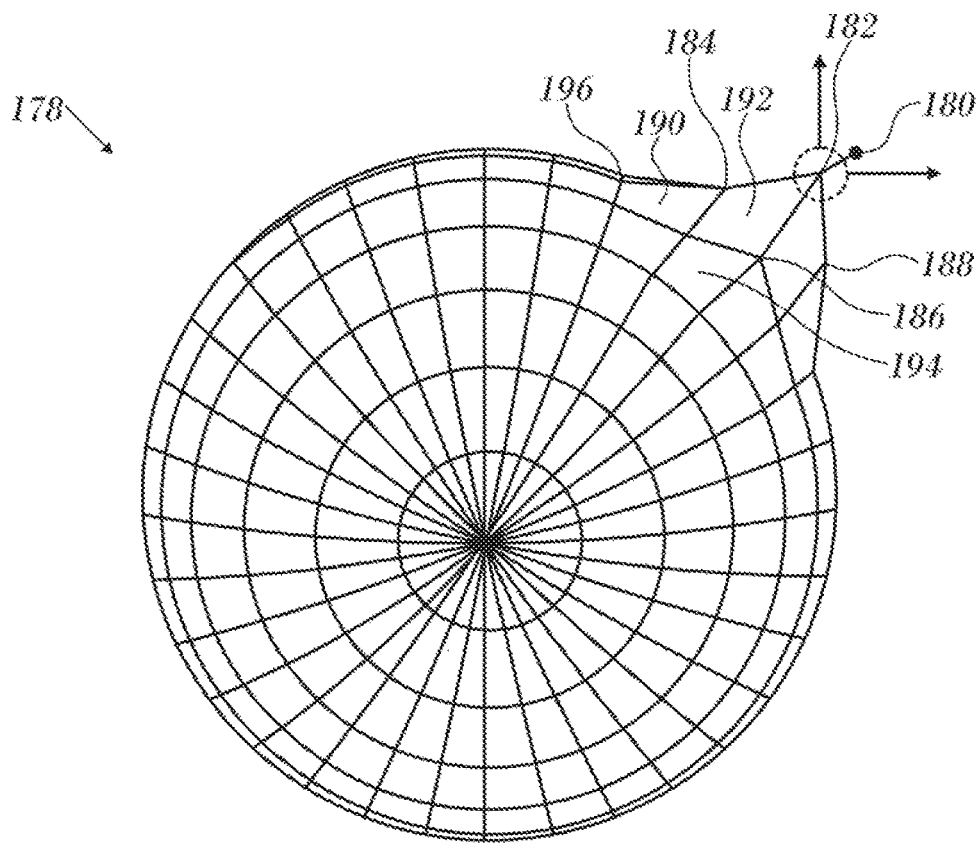
FIG. 9 shows the matrix of FIG. 8 following a displacement of vertices in accordance with an embodiment of the invention.

FIG. 8 illustrates the relationship between the mapped point 180 and vertex 182 prior to the first vertex shift in step 155 (FIG. 6). FIG. 9 shows matrix 178 after performance of step 155 (the effects are intentionally exaggerated for clarity). Vertex 182 has now been displaced toward mapped point 180. Neighboring vertices 184, 186, 188 are also influenced by proximity to mapped point 180 and hence are displaced toward mapped point 180. The displacements of vertices 184, 186, 188 are less than that of vertex 182, as they are more distant from the mapped point 180, and their assigned weights in step 148 (FIG. 6) are correspondingly lower than that of vertex 182.

An effect of the displacements is to draw vertices 184, 186, 188 away from vertices that are even more distant from mapped point 180, as evidenced by the difference in relationship between vertex 184 and distant vertex 196 in FIG. 8 and FIG. 9, and also by distortion of areas 190, 192, 194 in FIG. 9. Vertex 196 is unaffected by mapped point 180 and would be ignored in decision step 146 (FIG. 6).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising:
   a probe having a plurality of electrodes and adapted for insertion into a heart of a living subject; and
   a processor, which is configured to receive an electrical signal from the electrodes and to perform the steps of:
   constructing a position map of the electrodes, the position map having mapped points and simulating a 3-dimensional surface of the living subject's heart;
   placing the position map in registration with an acquired image of the living subject's heart;
   constructing, based on the position map, a realtime mesh of the living subject's heart that models the 3-dimensional surface of the living subject's heart, the realtime mesh having vertices; and
   adjusting positions of the vertices relative to the mapped points to improve a registration of the realtime mesh with the acquired image.

2. The apparatus according to claim 1, wherein the realtime mesh is a triangular matrix.

3. The apparatus according to claim 1, wherein adjusting positions of the vertices comprises the steps of:
   selecting a mapped point;
   identifying all vertices of the realtime mesh that are within a predetermined distance from a selected mapped point;
   calculating respective weight factors based on distances between the identified vertices and the selected mapped point;
   calculating new positions for the identified vertices comprising a shift toward the selected mapped point according to the respective weight factors; and
   defining a new mesh based on the new positions.

4. The apparatus according to claim 3, wherein the respective weight factors are calculated according to an inverse square of the distances between the identified vertices and the selected mapped point.

5. The apparatus according to claim 3, wherein the new positions are determined as vector sums of shifts toward respective mapped points determined in performances of the steps of identifying all vertices and calculating new positions.

6. The apparatus according to claim 3, wherein the distances between the identified vertices and the selected mapped point are geodesic distances.

7. A computer software product including a non-transitory computer-readable storage medium in which computer program instructions are stored, which instructions, when executed by a computer, cause the computer to perform the steps of:

receiving an electrical signal from a plurality of electrodes in a patient's heart and to perform the steps of:

constructing a position map of the electrodes, the position map having mapped points and simulating a 3-dimensional surface of the patient's heart;

placing the position map in registration with an acquired image of the heart;

constructing, based on the position map, a realtime mesh of the patient's heart that models the 3-dimensional surface of the patient's heart, the mesh having vertices; and adjusting positions of the vertices relative to the mapped points to improve a registration of the realtime mesh with the acquired image.

8. The computer software product according to claim 7, wherein the realtime mesh is a triangular matrix.

9. The computer software product according to claim 7, wherein adjusting positions of the vertices comprises the steps of:

selecting a mapped point;

identifying all vertices of the realtime mesh that are within a predetermined distance from a selected mapped point;

calculating respective weight factors based on distances between the identified vertices and the selected mapped point;

calculating new positions for the identified vertices comprising a shift toward the selected mapped point according to the respective weight factors; and defining a new mesh based on the new positions.

10. The computer software product according to claim 9, wherein the respective weight factors are calculated according to an inverse square of the distances between the identified vertices and the selected mapped point.

11. The computer software product according to claim 9, wherein the new positions are determined as vector sums of shifts toward respective mapped points determined in performances of the steps of identifying all vertices and calculating new positions.

12. The computer software product according to claim 9, wherein the distances between the identified vertices and the selected mapped point are geodesic distances.

13. A method, comprising the steps of:

inserting a probe having mapping electrodes into a patient's heart;

constructing a position map of the mapping electrodes, the position map having mapped points and simulating a 3-dimensional surface of the patient's heart;

placing the position map in registration with an acquired image of the patient's heart;

constructing, based on the position map, a realtime mesh of the patient's heart that models the 3-dimensional surface of the patient's heart, the realtime mesh having vertices; and adjusting positions of the vertices relative to the mapped points to improve a registration of the realtime mesh with the acquired image of the patient's heart.

14. The method according to claim 13, wherein the realtime mesh is a triangular matrix.

15. The method according to claim 13, wherein adjusting positions of the vertices comprising the steps of:

selecting a mapped point;

identifying all vertices of the realtime mesh that are within a predetermined distance from a selected mapped point;

calculating respective weight factors based on distances between the identified vertices and the selected mapped point;

calculating new positions for the identified vertices comprising a shift toward the selected mapped point according to the respective weight factors; and defining a new mesh based on the new positions.

16. The method according to claim 15, wherein the respective weight factors are calculated according to an inverse square of the distances between the identified vertices and the selected mapped point.

17. The method according to claim 15, wherein the new positions are determined as vector sums of shifts toward respective mapped points determined in performances of the steps of identifying all vertices and calculating new positions.

18. The method according to claim 15, wherein the distances between the identified vertices and the selected mapped point are geodesic distances.

19. The method according to claim 13, wherein inserting a probe comprises ascertaining tissue contact of the electrodes and a wall of the heart.

* * * * *